Figure 1:
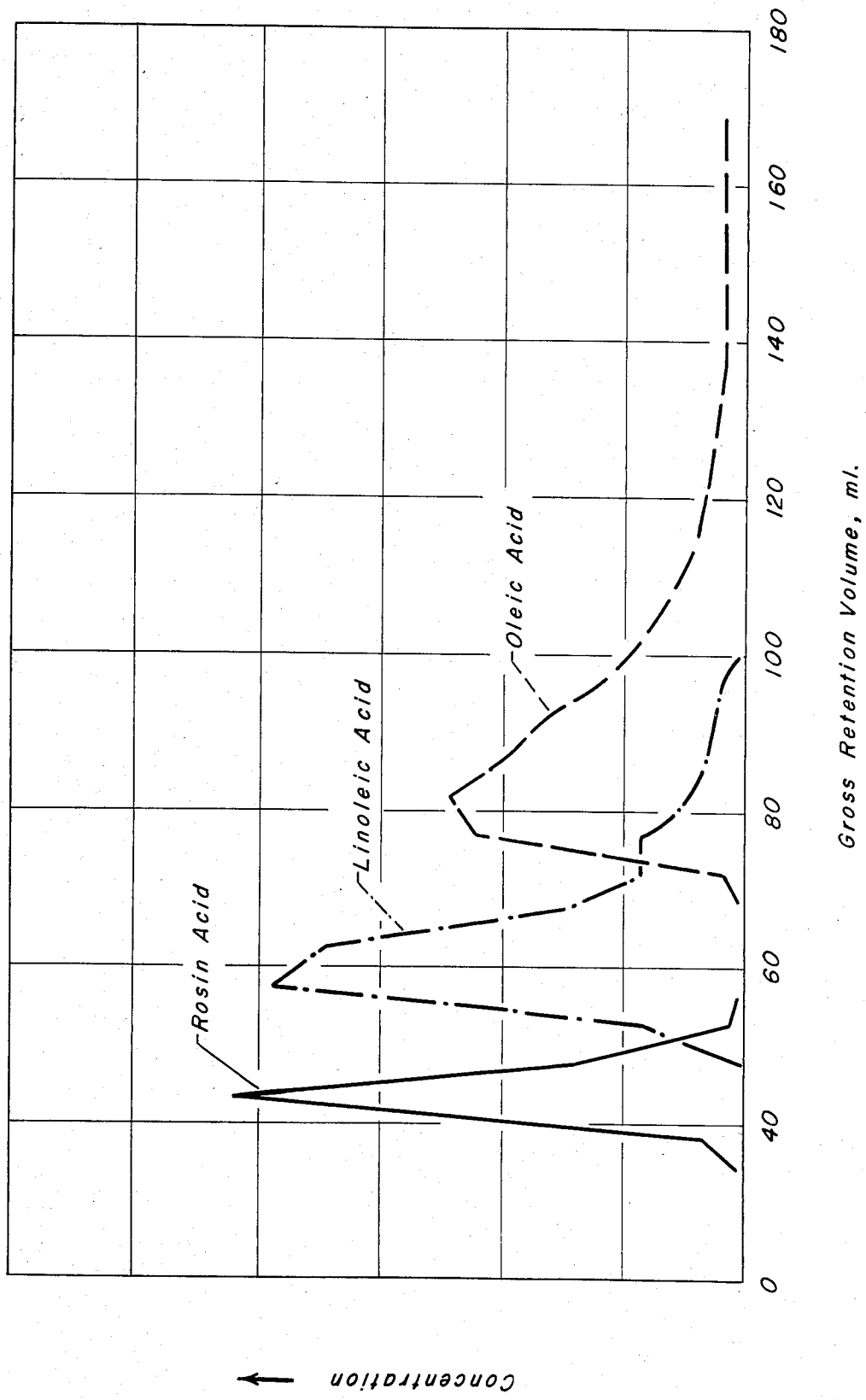

United States Patent [19]

Cleary et al.

[11] Patent Number: 4,524,030

[45] Date of Patent: Jun. 18, 1985

[54] PROCESS FOR SEPARATING FATTY ACIDS

[75] Inventors: Michael T. Cleary, Elmhurst; Santi Kulprathipanja, Hoffman Estates; Richard W. Neuzil, Downers Grove, all of Ill.

[73] Assignee: UOP Inc., Des Plaines, Ill.

[21] Appl. No.: 539,859

[22] Filed: Oct. 7, 1983

Related U.S. Application Data

[63] Continuation-in-part of Ser. No. 474,999, Mar. 14, 1983, , which is a continuation-in-part of Ser. No. 407,672, Aug. 12, 1982, Pat. No. 4,404,145, which is a continuation-in-part of Ser. No. 333,250, Dec. 21, 1981, abandoned, which is a continuation-in-part of Ser. No. 297,453, Aug. 28, 1981, abandoned, which is a continuation-in-part of Ser. No. 252,745, Apr. 10, 1981, Pat. No. 4,329,280.

[51] Int. Cl.$^3$ ............................................. C11C 1/08
[52] U.S. Cl. ........................... 260/419; 260/97.6; 260/97.7; 260/412.8; 260/420; 260/428; 260/428.5
[58] Field of Search ............... 260/97.6, 97.7, 419, 260/420, 428, 428.5, 412.8

[56] References Cited

U.S. PATENT DOCUMENTS

| | | | |
|---|---|---|---|
| 2,985,589 | 5/1961 | Broughton et al. | 210/34 |
| 3,114,782 | 12/1963 | Fleck et al. | 260/674 |
| 3,201,491 | 8/1965 | Stine et al. | 260/676 |
| 3,265,750 | 8/1966 | Peck et al. | 260/666 |
| 3,510,423 | 4/1968 | Neuzil et al. | 208/310 |
| 3,558,730 | 1/1971 | Neuzil | 260/674 |
| 3,558,732 | 1/1971 | Neuzil | 260/674 |
| 3,626,020 | 3/1969 | Neuzil | 260/674 SA |
| 3,663,638 | 5/1972 | Neuzil | 260/674 SA |
| 3,668,267 | 6/1972 | Hedge | 260/674 SA |
| 3,734,974 | 5/1973 | Neuzil | 260/674 SA |
| 3,864,416 | 2/1975 | Campbell et al. | 260/674 A |
| 4,048,205 | 9/1977 | Neuzil et al. | 260/428 |

*Primary Examiner*—Helen M. S. Sneed
*Attorney, Agent, or Firm*—William H. Page, II; Louis A. Morris

[57] ABSTRACT

This invention comprises a process for separating a fatty acid from a mixture comprising a fatty acid and a rosin acid, which process comprises contacting the mixture at separation conditions with a molecular sieve comprising a crystalline silica, thereby selectively retaining the fatty acid. The fatty acid is recovered from the molecular sieve by displacement with a displacement fluid comprising an ester containing less than six carbon atoms per molecule. Once the rosin acid is removed from the feed mixture, the process is also effective in separating the fatty acids from each other, using the same molecular sieve and displacement fluid.

10 Claims, 2 Drawing Figures

PROCESS FOR SEPARATING FATTY ACIDS

CROSS-REFERENCE TO RELATED APPLICATIONS

This application is a continuation-in-part of prior copending application Ser. No. 474,999, filed Mar. 14, 1983, which is a continuation-in-part of prior copending application Ser. No. 407,672, filed Aug. 12, 1982, now U.S. Pat. No. 4,404,145, which is a Continuation-in-Part of prior copending application Ser. No. 333,250 filed Dec. 21, 1981 and now abandoned, which is a Continuation-in-Part of prior copending application Ser. No. 297,453 filed Aug. 28, 1981 and now abandoned, which is a Continuation-in-Part of prior copending application Ser. No. 252,745 filed Apr. 10, 1981, now U.S. Pat. No. 4,329,280, all of which prior applications are incorporated herein by reference.

BACKGROUND OF THE INVENTION

1. Field of the Invention

The field of art to which this invention pertains is the solid bed molecular sieve separation of fatty acids. More specifically, the invention relates to a process for separating a fatty acid from a rosin acid and fatty acids from each other, which process employs a molecular sieve comprising crystalline silica and a specific displacement fluid.

2. Background Information

It is well known in the separation art that certain crystalline aluminosilicates can be used to separate hydrocarbon types from mixtures thereof. As a few examples, a separation process disclosed in U.S. Pat. Nos. 2,985,589 and 3,201,491 uses a type A zeolite to separate normal paraffins from branched chain paraffins, and processes described in U.S. Pat. Nos. 3,265,750 and 3,510,423 use type X or type Y zeolites to separate olefinic hydrocarbons from paraffinic hydrocarbons. In addition to their use in processes for separating hydrocarbon types, X and Y zeolites have been employed in processes to separate individual hydrocarbon isomers. As a few examples, adsorbents comprising X and Y zeolites are used in the process described in U.S. Pat. No. 3,114,782 to separate alkyl-trisubstituted benzene isomers; in the process described in U.S. Pat. No. 3,864,416 to separate alkyl-tetrasubstituted monocyclic aromatic isomers; and in the process described in U.S. Pat. No. 3,668,267 to separate specific alkyl-substituted naphthalenes. Because of the commercial importance of paraxylene, perhaps the more well-known and extensively used hydrocarbon isomer separation processes are those for separating paraxylene from a mixture of $C_8$ aromatics. In processes described in U.S. Pat. Nos. 3,558,730; 3,558,732; 3,626,020; 3,663,638; and 3,734,974, for example, adsorbents comprising particular zeolites are used to separate paraxylene from feed mixtures comprising paraxylene and at least one other xylene isomer by selectively adsorbing paraxylene over the other xylene isomers.

In contrast, this invention relates to the separation of non-hydrocarbons and more specifically to the separation of fatty acids. Substantial uses of fatty acids are in the plasticizer and surface active agent fields. Derivatives of fatty acids are of value in compounding lubricating oil, as a lubricant for the textile and molding trade, in special lacquers, as a waterproofing agent, in the cosmetic and pharmaceutical fields, and in biodegradable detergents.

It is known from U.S. Pat. No. 4,048,205 to use type X and type Y zeolites for the separation of unsaturated from saturated esters of fatty acids. The type X and type Y zeolites, however, will not separate the esters of rosin acids found in tall oil from the esters of fatty acids nor the free acids, apparently because the pore sizes of those zeolites (over 7 angstroms) are large enough to accommodate and retain the relatively large diameter molecules of esters of rosin acids as well as the smaller diameter molecules of esters of fatty acids (as well as the respective free acids). Type A zeolite, on the other hand, has a pore size (about 5 angstroms) which is unable to accommodate either of the above type esters (or free acids) and is, therefore, unable to separate them. An additional problem when a zeolite is used to separate free acids is the reactivity between the zeolite and free acids.

We have discovered that crystalline silica is uniquely suitable for the separation process of this invention in that it exhibits acceptance for a fatty acid with respect to a rosin acid, particularly when used with a specific displacement fluid comprising an ester having less than six carbon atoms per molecule, and does not exhibit reactivity with the free acids.

SUMMARY OF THE INVENTION

In brief summary, the invention is, in one embodiment, a process for separating a fatty acid from a feed mixture comprising a fatty acid and a rosin acid. The feed mixture is contacted at separation conditions with a molecular sieve comprising crystalline silicalite having a silica to alumina mole ratio of at least 12, thereby selectively retaining said fatty acid. The rosin acid is then removed from fatty acid containing molecular sieve and the fatty acid recovered by displacement at displacement conditions with a displacement fluid comprising an ester containing less than six carbon atoms per molecule.

In another embodiment, the present invention comprises a process for separating oleic acid from linoleic acid contained in a feed mixture comprising the acids. The process comprises contacting the feed mixture at separation conditions with a molecular sieve comprising a crystalline silica having a silica to alumina mole ratio of at least 12, thereby selectively retaining the oleic acid, removing linoleic acid from the oleic acid containing molecular sieve, and recovering the oleic acid from the molecular sieve by displacement at displacement conditions, with a displacement fluid comprising an ester containing less than six carbon atoms per molecule.

Other embodiments of our invention encompass details about feed mixtures, molecular sieves, displacement fluids, flow schemes, and operating conditions, all of which are hereinafter disclosed in the following discussions of each of the facets of the present invention.

DESCRIPTION OF THE INVENTION

At the outset the definitions of various terms used throughout the specification will be useful in making clear the operation, objects and advantages of our process.

A "feed mixture" is a mixture containing one or more extract components and one or more raffinate components to be separated by our process. The term "feed stream" indicates a stream of a feed mixture which passes to the molecular sieve used in the process.

An "extract component" is a compound or type of compound that is retained by the molecular sieve while a "raffinate component" is a compound or type of compound that is not retained. In this process, a fatty acid is an extract component and a rosin acid is a raffinate component. The term "displacement fluid" shall mean generally a fluid capable of displacing an extract component. The term "displacement fluid stream" or "displacement fluid input stream" indicates the stream through which displacement fluid passes to the molecular sieve. The term "diluent" or "diluent stream" indicates the stream through which diluent passes to the molecular sieve. The term "raffinate stream" or "raffinate output stream" means a stream through which a raffinate component is removed from the molecular sieve. The composition of the raffinate stream can vary from essentially a 100% displacement fluid to essentially 100% raffinate components. The term "extract stream" or "extract output stream" shall mean a stream through which an extract material which has been displaced by a displacement fluid is removed from the molecular sieve. The composition of the extract stream, likewise, can vary from essentially 100% displacement fluid to essentially 100% extract components. At least a portion of the extract stream and preferably at least a portion of the raffinate stream from the separation process are passed to separation means, typically fractionators, where at least a portion of displacement fluid and diluent is separated to produce an extract product and a raffinate product. The terms "extract product" and "raffinate product" mean products produced by the process containing, respectively, an extract component and a raffinate component in higher concentrations than those found in the extract stream and the raffinate stream. Although it is possible by the process of this invention to produce a high purity, fatty acid product or rosin acid product (or both) at high recoveries, it will be appreciated that an extract component is never completely retained by the molecular sieve, nor is a raffinate component completely not retained by the molecular sieve. Therefore, varying amounts of a raffinate component can appear in the extract stream and, likewise, varying amounts of an extract component can appear in the raffinate stream. The extract and raffinate streams then are further distinguished from each other and from the feed mixture by the ratio of the concentrations of an extract component and a raffinate component appearing in the particular stream. More specifically, the ratio of the concentration of a fatty acid to that of non-retained rosin acid or other fatty acid will be lowest in the raffinate stream, next highest in the feed mixture, and the highest in the extract stream. Likewise, the ratio of the concentration of rosin acid or non-retained fatty acid to that of the retained fatty acid will be highest in the raffinate stream, next highest in the feed mixture, and the lowest in the extract stream.

The term "selective pore volume" of the molecular sieve is defined as the volume of the molecular sieve which selectively retains an extract component from the feed mixture. The term "non-selective void volume" of the molecular sieve is the volume of the molecular sieve which does not selectively retain an extract component from the feed mixture. This volume includes the cavities of the molecular sieve which admit raffinate components and the interstitial void spaces between molecular sieve particles. The selective pore volume and the non-selective void volume are generally expressed in volumetric quantities and are of importance in determining the proper flow rates of fluid required to be passed into an operational zone for efficient operations to take place for a given quantity of molecular sieve. When molecular sieve "passes" into an operational zone (hereinafter defined and described) employed in one embodiment of this process, its non-selective void volume together with its selective pore volume carries fluid into that zone. The non-selective void volume is utilized in determining the amount of fluid which should pass into the same zone in a countercurrent direction to the molecular sieve to displace the fluid present in the non-selective void voluae. If the fluid flow rate passing into a zone is smaller than the non-selective void volume rate of molecular sieve material passing into that zone, there is a net entrainment of liquid into the zone by the molecular sieve. Since this net entrainment is a fluid present in the non-selective void volume of the molecular sieve, it in most instances comprises non-retained feed components.

Before considering feed mixtures which can be charged to the process of this invention, brief reference is first made to the terminology and to the general production of fatty acids. The fatty acids are a large group of aliphatic monocarboxylic acids, many of which occur as glycerides (esters of glycerol) in natural fats and oils. Although the term "fatty acids" has been restricted by some to the saturated acids of the acetic acid series, both normal and branched chain, it is now generally used, and is so used herein, to include also related unsaturated acids, certain substituted acids, and even aliphatic acids containing alicyclic substituents. The naturally occurring fatty acids with a few exceptions are higher straight chain unsubstituted acids containing an even number of carbon atoms. The unsaturated fatty acids can be divided, on the basis of the number of double bonds in the hydrocarbon chain, into monoethanoid, diethanoid, triethanoid, etc. (or monoethylenic, etc.). Thus the term "unsaturated fatty acid" is a generic term for a fatty acid having at least one double bond, and the term "polyethanoid fatty acid" means a fatty acid having more than one double bond per molecule. Fatty acids are typically prepared from glyceride fats or oils by one of several "splitting" or hydrolytic processes. In all cases, the hydrolysis reaction may be summarized as the reaction of a fat or oil with water to yield fatty acids plus glycerol. In modern fatty acid plants this process is carried out by continuous high pressure, high temperature hydrolysis of the fat. Starting materials commonly used for the production of fatty acids include coconut oil, palm oil, inedible animal fats, and the commonly used vegetable oils, soybean oil, cottonseed oil and corn oil.

The source of fatty acids with which the present invention is primarily concerned is tall oil, a by-product of the wood pulp industry, usually recovered from pine wood "black liquor" of the sulfate or Kraft paper process. Tall oil contains about 50–60% fatty acids and about 34–40% rosin acids. The fatty acids include oleic, linoleic, palmitic and stearic acids. Rosin acids, such as abietic acid, are monocarboxylic acids having a molecular structure comprising carbon, hydrogen and oxygen with three fused six-membered carbon rings, which accounts for the much larger molecular diameter of rosin acids as compared to fatty acids.

Feed mixtures which can be charged to our process may contain, in addition to the components of tall oil, a diluent material that is not adsorbed by the adsorbent and which is preferably separable from the extract and raffinate output stream by fractional distillation. When a diluent is employed, the concentration of diluent in the mixture of diluent and acids will preferably be from a few vol. % up to about 80 vol. % with the remainder being fatty acids and rosin acids. The usual diluent comprises displacement material.

Displacement fluids used in various prior art adsorptive and molecular sieve separation processes vary depending upon such factors as the type of operation employed. In separation processes which are generally operated continuously at substantially constant pressures and temperatures to ensure liquid phase, and which employ a molecular sieve, the displacement material must be judiciously selected to satisfy many criteria. First, the displacement material should displace an extract component from the molecular sieve with reasonable mass flow rates but yet allow access of an extract component into the molecular sieve so as not to unduly prevent an extract component from displacing the displacement material in a following separation cycle. Displacement fluids should additionally be substances which are easily separable from the feed mixture that is passed into the process. Both the raffinate stream and the extract stream are removed from the molecular sieve in admixture with displacement fluid and without a method of separating at least a portion of the displacement fluid, the purity of the extract product and the raffinate product would not be very high nor would the displacement fluid be available for reuse in the process. It is therefore contemplated that any displacement fluid material used in this process would preferably have a substantially different average boiling point than that of the feed mixture to allow separation of at least a portion of displacement fluid from feed components in the extract and raffinate streams by simple fractional distillation, thereby permitting reuse of displacement fluid in the process. The term "substantially different" as used herein shall mean that the difference between the average boiling points between the displacement fluid and the feed mixture shall be at least about 5° C. The boiling range of the displacement fluid may be higher or lower than that of the feed mixture. Finally, displacement fluids should also be materials which are readily available and therefore reasonable in cost. In the preferred isothermal, isobaric, liquid-phase operation of the process of our invention, we have found the optimum displacement fluid as discussed hereinafter, to be an ester containing less than six carbon atoms per molecule.

It has been observed that even a crystalline silica may be ineffective in separating fatty and rosin acids upon reuse of the molecular sieve bed for separation following the displacement step. When displacement fluid is present in the bed, selective retention of the fatty acid may not occur. It is hypothesized that the displacement fluid takes part in or even catalyzes hydrogen-bonded dimerization reactions in which there is an alignment between the molecules of the fatty and rosin acids and, perhaps, the molecules of the displacement fluid. These dimerization reactions may be represented by the formulas:

$$FA + FA \rightleftharpoons (FAFA)$$

$$RA + RA \rightleftharpoons (RARA)$$

$$FA + RA \rightleftharpoons (FARA)$$

where FA and RA stand for fatty acids and rosin acids, respectively. There are certain displacement fluids such as organic acids, which, if used, would probably also be reactants and product constituents in the above equations. The dimers would preclude separation of the fatty and rosin acids by blocking access of the former into the pores of the molecular sieve. This hindrance to separation caused by the presence of dimers does not appear to be a significant problem in the aforementioned process for separation of esters of fatty and rosin acids.

We previously discovered that the above dimerization reactions could be minimized, at least to the extent required to enable separation of the rosin and fatty acids, by first flushing the molecular sieve with a suitable diluent. The diluent served to remove displacement fluid at least from the non-selective void volume of the molecular sieves. Proper selection required solubility of the feed stream components in the diluent as well as easy separation of the diluent by conventional means, as with the displacement fluid. The pre-flush step obviously added a degree of complication to the separation process.

We then discovered that the above pre-flush was unnecessary if the displacement fluid comprised an organic acid in solution with a properly selected diluent. There are diluents which exhibit the property of minimizing dimerization. The measure of this property was found to be the polarity index of the liquid. Polarity index is as described in the article, "Classification of the Solvent Properties of Common Liquids"; Snyder, L. J. Chromatography, 92, 223 (1974), incorporated herein by reference. The minimum required polarity index of the displacement fluid-diluent was found to be 3.5, when the displacement fluid used was a short chain organic acid as discussed above. The diluent was required to comprise from about 50 to about 95 liquid volume percent of the displacement fluid. Polarity indexes for certain selected diluents are as follows:

| SOLVENT | POLARITY INDEX |
| --- | --- |
| Isooctane | −0.4 |
| n-Hexane | 0.0 |
| Toluene | 2.3 |
| p-Xylene | 2.4 |
| Benzene | 3.0 |
| Methylethylketone | 4.5 |
| Acetone | 5.4 |

We then found that an effective displacement fluid is a solution of water soluble high polarity index material, i.e., light ketones, and water. It should be realized that the polarity index of water is 9.0 and, therefore, a blend of water and, for example, acetone has a very high polarity index since the polarity indexes of the components of such a blend are additive, i.e., the polarity index of a 50—50 of acetone and water would be equal to: $0.5 \times 5.4 + 0.5 \times 9.0 = 7.2$. The ketone not only contributed to polarity index but, equally important, was soluble in the tall oil feedstock. We have recently found, however, that even ketones are not perfect displacement materials. For example, analytical results have shown that acetone does undergo some aldol condensation during pulse testing and pilot plant evaluation as illustrated by the following reactions:

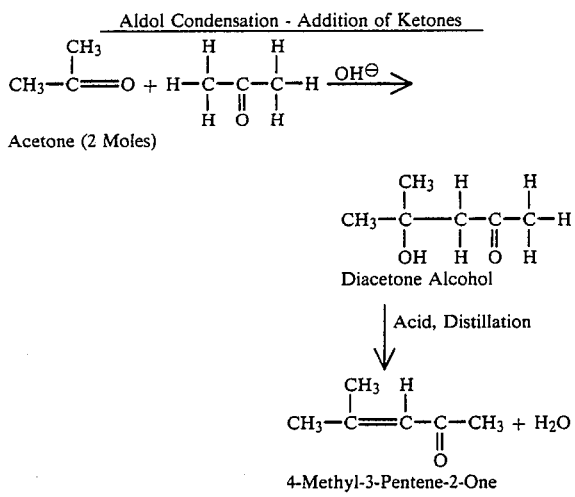

Acetone (2 Moles)

Diacetone Alcohol

4-Methyl-3-Pentene-2-One

The condensation products would, of course, tend to block access to molecular sieve openings. Esters do not exhibit condensation reactions such as the above.

The molecular sieve to be used in the process of this invention comprises crystalline silica having a silica/alumina mole ratio of at least 12. One such crystalline silica is known as silicalite which has a silica/alumina mole ratio of infinity, i.e., it contains no alumina. Silicalite is a hydrophobic crystalline silica molecular sieve. Silicalite is disclosed and claimed in U.S. Pat. Nos. 4,061,724 and 4,104,294 to Grose et al, incorporated herein by reference. Due to its aluminum-free structure, silicalite does not show ion-exchange behavior, and is hydrophobic and organophilic. Silicalite is uniquely suitable for the separation process of this invention for the presumed reason that its pores are of a size and shape that enable the silicalite to function as a molecular sieve, i.e., accept the molecules of fatty acids into its channels or internal structure, while rejecting the molecules of rosin acids. A more detailed discussion of silicalite may be found in the article, "Silicalite, A New Hydrophobic Crystalline Silica Molecular Sieve"; Nature, Vol. 271, Feb. 9, 1978, incorporated herein by reference.

Examples of other crystalline silicas suitable for use in the present invention are those having the trademark designation "ZSM" and silica/alumina mole ratios of at least 12. The ZSM adsorbents are as described in U.S. Pat. No. 4,309,281 to Dessau, incorporated herein by reference. The crystalline framework and channel structure of silicalite may vary, the two forms being referred to as silicalite-1 (a combination of linear and zig-zag channels) and silicalite-2 (linear channels). ZSM analogues of silicalite-1 and silicalite-2 are ZSM-5 and ZSM-11, respectively.

Typically, adsorbents used in separative processes contain the crystalline material dispersed in an amorphous material or inorganic matrix, having channels and cavities therein which enable liquid access to the crystalline. The binder aids in forming or agglomerating the crystalline particles which otherwise would comprise a fine powder. The molecular sieve may thus be in the form of particles such as extrudates, aggregates, tablets, macrospheres or granules having a desired particle range, preferably from about 16 to about 60 mesh (Standard U.S. Mesh). Colloidal amorphous silica is an ideal binder for crystalline silica in that like the crystalline silica itself this binder exhibits no reactivity for the free fatty acids. A preferred silica is marketed by DuPont Company under the trademark "Ludox". The crystalline silica powder is dispersed in the Ludox which is then gelled and treated in a manner so as to substantially eliminate hydroxyl groups, such as by thermal treatment in the presence of oxygen at a temperature from about 450° to about 1000° C. for a minimum period from about 3 hours to about 48 hours. The crystalline silica should be present in the silica matrix in amounts ranging from about 75 wt. % to about 98 wt. % silicate based on volatile free composition.

The molecular sieve may be employed in the form of a dense compact fixed bed which is alternatively contacted with the feed mixture and displacement fluid. In the simplest embodiment of the invention, the molecular sieve is employed in the form of a single static bed in which case the process is only semi-continuous. In another embodiment, a set of two or more static beds may be employed in fixed bed contacting with appropriate valving so that the feed mixture is passed through one or more molecular sieve beds, while the displacement fluid can be passed through one or more of the other beds in the set. The flow of feed mixture and displacement fluid may be either up or down through the molecular sieve. Any of the conventional apparatus employed in static bed fluid-solid contacting may be used.

Moving bed or simulated moving bed flow systems, however, have a much greater separation efficiency than fixed bed systems and are therefore preferred. In the moving bed or simulated moving bed processes, the retention and displacement operations are continuously taking place which allows both continuous production of an extract and a raffinate stream and the continual use of feed and displacement fluid streams. One preferred embodiment of this process utilizes what is known in the art as the simulated moving bed countercurrent flow system. The operating principles and sequence of such a flow system are described in U.S. Pat. No. 2,985,589, incorporated herein by reference. In such a system, it is the progressive movement of multiple liquid access points down a molecular sieve chamber that simulates the upward movement of molecular sieve contained in the chamber. Reference can also be made to D. B. Broughton U.S. Pat. No. 2,985,589 and to a paper entitled, "Continuous Adsorptive Processing—A New Separation Technique" by D. B. Broughton presented at the 34th Annual Meeting of the Society of Chemical Engineers at Tokyo, Japan on Apr. 2, 1969, both references incorporated herein by reference, for further explanation of the simulated moving bed countercurrent process flow scheae.

Another embodiment of a simulated moving bed flow system suitable for use in the process of the present invention is the cocurrent high efficiency simulated moving bed process disclosed in U.S. Pat. No. 4,402,832, incorporated by reference herein in its entirety.

It is contemplated that at least a portion of the extract output stream will pass into a separation means wherein at least a portion of the displacement fluid can be separated to produce an extract product containing a reduced concentration of displacement fluid. Preferably, but not necessary to the operation of the process, at least a portion of the raffinate output stream will also be passed to a separation means wherein at least a portion of the displacement fluid can be separated to produce a displacement fluid stream which can be reused in the process and a raffinate product containing a reduced concentration of displacement fluid. The separation means will typically be a fractionation column, the design and operation of which is well known to the separation art.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Separation conditions will include a temperature range of from about 90° C. to about 140° C. with about 120° C. being more preferred and a pressure sufficient to maintain liquid-phase. Displacement conditions will include the same range of temperatures and pressures as used for separation conditions.

The size of the units which can utilize the process of this invention can vary anywhere from those of pilot-plant scale (see for example U.S. Pat. No. 3,706,812) to those of commercial scale and can range in flow rates from as little as a few cc an hour up to many thousands of gallons per hour.

A dynamic testing apparatus is employed to test various molecular sieves with a particular feed mixture and displacement fluid to measure the molecular sieve characteristics of retention capacity and exchange rate. The apparatus consists of a helical molecular sieve chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the molecular sieve chamber. A pulse test, performed using this apparatus and the following general procedure, is used to determine data for various molecular sieve systems. The molecular sieve is filled to equilibrium with a particular displacement fluid material by passing the displacement fluid through the molecular sieve chamber. At a convenient time, a 5 ml pulse of feed containing known concentrations of a particular extract component or of a raffinate component or both, all diluted in displacement fluid, is injected for a duration of several minutes. Displacement fluid flow is resumed, and the extract component or the raffinate component (or both) are eluted as in a liquid-solid chromatographic operation. The effluent can be analyzed on-stream or alternatively, effluent samples can be collected periodically and later analyzed separately by analytical equipment and traces of the envelopes or corresponding component peaks developed.

From information derived from the test, molecular sieve performance can be rated in terms of void volume, retention volume for an extract or a raffinate component, and the rate of displacement of an extract component from the molecular sieve. The retention volume of an extract or a raffinate component may be characterized by the distance between the center of the peak envelope of the extract or raffinate component, respectively, and the peak envelopes of a tracer component or some other known reference point. It is expressed in terms of the volume in cubic centimeters of displacement fluid pumped during this time interval represented by the distance between the peak envelopes. The rate of exchange of an extract component with the displacement fluid can generally be characterized by the width of the peak envelopes at half intensity. The narrower the peak width, the faster the displacement rate. The displacement rate can also be characterized by the distance between the center of a tracer peak envelope and the disappearance of an extract component which has just been displaced. This distance is again the volume of displacement fluid pumped during this time interval.

The following non-limiting examples are presented to illustrate the process of the present invention and are not intended to unduly restrict the scope of the claims attached hereto.

EXAMPLE I

The above described pulse test apparatus was used to obtain data for this example. The liquid temperature was 120° C. and the flow was down the column at the rate of 1.2 ml/min. The feed stream comprised 20 wt. % distilled tall oil, and 80 wt. % displacement fluid. The column was packed with 23 wt. % Ludox bound silicalite (77 wt. % silicalite-1) which had been prepared as preferred in the practice of the present invention. The displacement fluid used was ethylacetate.

The results of this example are shown on the accompanying FIG. 1. It is apparent from FIG. 1 that the separation achieved is quite good. The separation of the rosin acid from fatty acid curves is clear and distinct, as is the separation between the linoleic and oleic acid curves which is indicative of an ability to separate those two acids from each other in a second pass following removal of the rosin acids in a first pass. There was no indication of any condensation reaction as might be expected with a ketone displacement fluid, as discussed above.

EXAMPLE II

The pulse test of Example I was repeated except that the displacement fluid used was aethylpropionate.

Figure 2:
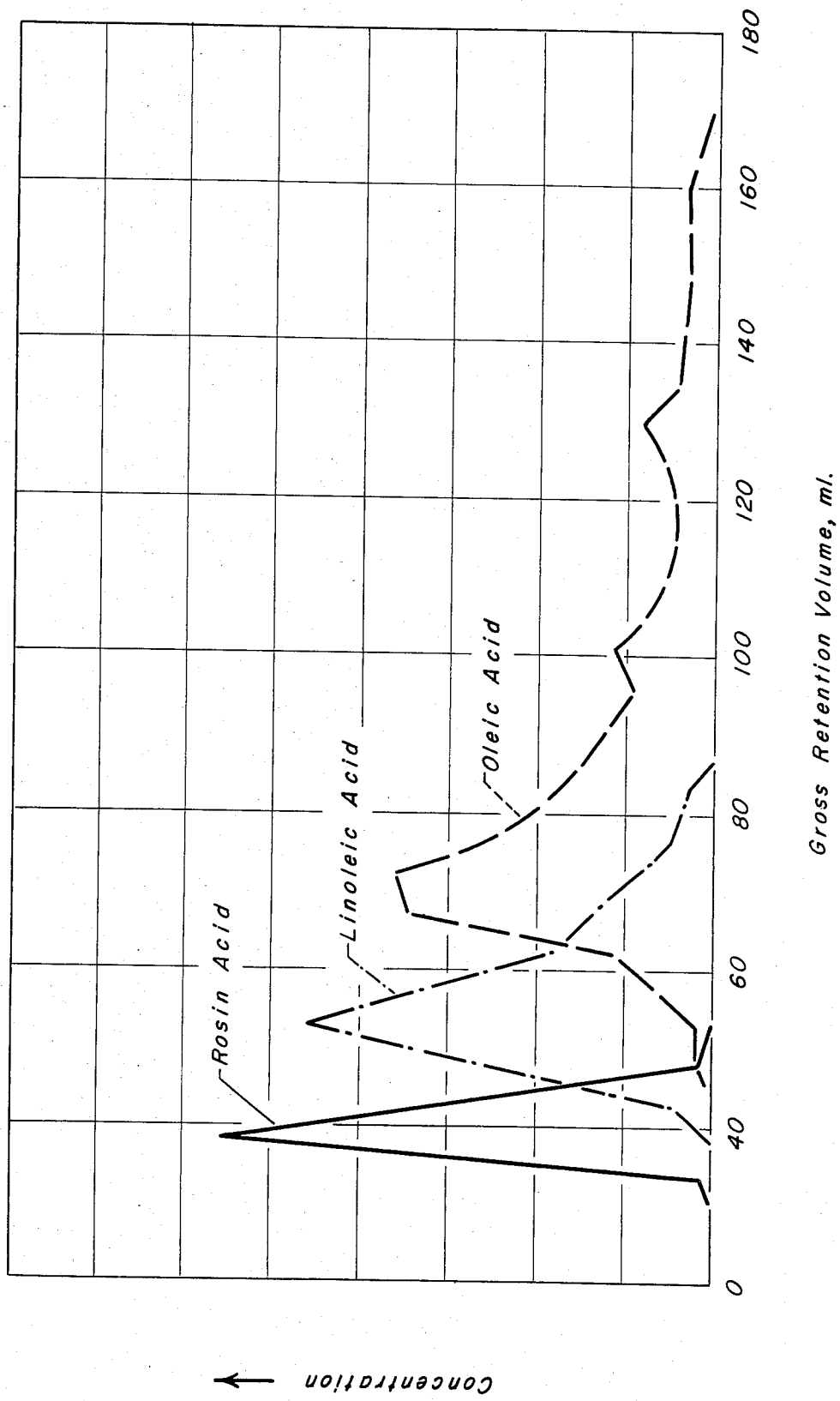

The results of this example are shown on accompanying FIG. 2. The separation achieved via the present invention is again illustrated.

We claim as our invention:

1. A process for separating a fatty acid from a feed mixture comprising a fatty acid and a rosin acid, said process comprising contacting said feed mixture at separation conditions with a molecular sieve comprising a crystalline silica having a silica to alumina mole ratio of at least 12, thereby selectively retaining said fatty acid, and removing rosin acid from the fatty acid containing molecular sieve, said fatty acid being recovered from said molecular sieve by displacement at displacement conditions with a displacement fluid comprising an ester containing less than six carbon atoms per molecule.

2. The process of claim 1 wherein said separation and displacement conditions include a temperature within the range of from about 90° C. to about 140° C. and a pressure sufficient to maintain liquid phase.

3. The process of claim 1 wherein said molecular sieve comprises crystalline silica in a silica matrix.

4. The process of claim 1 wherein said process is effected with a simulated moving-bed flow system.

5. The process of claim 4 wherein said simulated moving-bed flow system is of the countercurrent type.

6. The process of claim 4 wherein said simulated moving-bed flow system is of the co-current high efficiency type.

7. The process of claim 1 wherein said molecular sieve comprises silicalite.

8. A process for separating oleic acid from linoleic acid contained in a feed mixture comprising said acids, said process comprising contacting said feed mixture at separation conditions with a molecular sieve comprising a crystalline silica having a silica to alumina mole ratio of at least 12, thereby selectively retaining said oleic acid, removing linoleic acid from the oleic acid containing molecular sieve, and recovering said oleic acid from said molecular sieve by displacement at displacement conditions, with a displacement fluid comprising an ester containing less than six carbon atoms per molecule.

9. The process of claim 8 wherein said feed mixture contains a rosin acid and said process includes first contacting said feed mixture with a first molecular sieve comprising a crystalline silica having a silica to alumina mole ratio of at least 12, thereby selectively retaining said fatty acids to the exclusion of said rosin acid, removing said rosin acid from the fatty acids containing first molecular sieve, recovering a mixture of said fatty acids by displacement from said first molecular sieve and then contacting the fatty acid mixture with a second molecular sieve comprising the molecular sieve which effects the separation of the fatty acids from each other.

10. The process of claim 8 wherein said separation and displacement conditions include a temperature within the range of from about 90° C. to about 140° C. and a pressure sufficient to maintain liquid phase.

* * * * *